(12) United States Patent
Bosel et al.

(10) Patent No.: US 8,545,434 B2
(45) Date of Patent: Oct. 1, 2013

(54) CATHETER PORT CONFIGURATION

(75) Inventors: Christopher D. Bosel, Bloomington, IN (US); Drew P. Lyons, Bloomington, IN (US)

(73) Assignee: Cook Medical Technology LLC, Bloomington, IN (US)

( * ) Notice: Subject to any disclaimer, the term of this patent is extended or adjusted under 35 U.S.C. 154(b) by 393 days.

(21) Appl. No.: 11/877,057

(22) Filed: Oct. 23, 2007

(65) Prior Publication Data

US 2008/0103480 A1 May 1, 2008

Related U.S. Application Data

(60) Provisional application No. 60/854,515, filed on Oct. 26, 2006.

(51) Int. Cl.
*A61M 3/00* (2006.01)

(52) U.S. Cl.
USPC .......................................... 604/43; 604/523

(58) Field of Classification Search
USPC ................... 604/4.01, 29, 43, 173
See application file for complete search history.

(56) References Cited

U.S. PATENT DOCUMENTS

| | | | |
|---|---|---|---|
| 3,938,530 A | 2/1976 | Santomieri | 128/349 R |
| 3,946,741 A | 3/1976 | Adair | 128/347 |
| 4,129,129 A | 12/1978 | Amrine | 128/214 R |
| 4,134,402 A | 1/1979 | Mahurkar | 128/214 R |
| 4,154,242 A | 5/1979 | Termanini | 128/349 R |
| 4,493,696 A | 1/1985 | Uldall | 604/43 |
| RE31,855 E | 3/1985 | Osborne | 604/161 |
| 4,568,329 A | 2/1986 | Mahurkar | 604/43 |
| 4,581,025 A | 4/1986 | Timmermans | 604/264 |
| 4,583,968 A | 4/1986 | Mahurkar | 604/43 |
| 4,643,711 A | 2/1987 | Bates | 604/4 |
| 4,655,745 A | 4/1987 | Corbett | 604/49 |
| 4,680,029 A | 7/1987 | Ranford et al. | 604/280 |
| 4,692,141 A * | 9/1987 | Mahurkar | 604/43 |
| 4,733,669 A | 3/1988 | Segal | 128/663 |
| 4,772,268 A | 9/1988 | Bates | 604/174 |
| 4,808,163 A | 2/1989 | Laub | 604/105 |

(Continued)

FOREIGN PATENT DOCUMENTS

| | | |
|---|---|---|
| EP | 0 301 854 A2 | 2/1989 |
| WO | WO 01/19425 A1 | 3/2001 |

(Continued)

OTHER PUBLICATIONS

International Search Report and Written Opinion dated Jun. 4, 2008, from International Application No. PCT/US2007/082203.

*Primary Examiner* — Kevin C Sirmons
*Assistant Examiner* — Brandy S Lee
(74) *Attorney, Agent, or Firm* — Brinks Hofer Gilson & Lione

(57) ABSTRACT

A catheter for use in the extracorporeal treatment of bodily fluids comprises a catheter body having a withdrawal port, an infusion port, and a plurality of lumens therein. One of the lumens comprises a withdrawal lumen for transport of fluids withdrawn from a body vessel through the withdrawal port to an extracorporeal treatment unit, such as a dialyzer. Another lumen comprises an infusion lumen for infusion of treated fluids from the extracorporeal treatment unit through the infusion port into the vessel. The withdrawal port is positioned proximally from the infusion port along a length of the catheter body, and includes a generally helical profile.

15 Claims, 7 Drawing Sheets

(56) References Cited

U.S. PATENT DOCUMENTS

| | | | |
|---|---|---|---|
| 4,878,893 A | 11/1989 | Chin | 604/21 |
| 4,904,238 A | 2/1990 | Williams | 604/43 |
| 4,936,826 A | 6/1990 | Amarasinghe | 604/52 |
| 4,973,301 A | 11/1990 | Nissenkorn | 604/8 |
| 4,995,865 A | 2/1991 | Gahara et al. | 604/43 |
| 4,995,868 A | 2/1991 | Brazier | 604/105 |
| 5,106,368 A | 4/1992 | Uldall et al. | 604/43 |
| 5,156,597 A | 10/1992 | Verreet et al. | 604/175 |
| 5,193,533 A | 3/1993 | Body et al. | 128/207.14 |
| 5,221,256 A | 6/1993 | Mahurkar | 604/43 |
| 5,250,034 A | 10/1993 | Appling et al. | 604/164 |
| 5,275,610 A | 1/1994 | Eberbach | 606/198 |
| 5,352,198 A | 10/1994 | Goldenberg et al. | 604/95 |
| 5,360,397 A | 11/1994 | Pinchuk | 604/27 |
| 5,364,344 A | 11/1994 | Beattie et al. | 604/43 |
| 5,403,291 A | 4/1995 | Abrahamson | 604/280 |
| 5,409,460 A | 4/1995 | Krumme | 604/107 |
| 5,443,449 A | 8/1995 | Buelna | 604/105 |
| 5,486,159 A | 1/1996 | Mahurkar | 604/4 |
| 5,489,278 A | 2/1996 | Abrahamson | 604/280 |
| 5,509,897 A | 4/1996 | Twardowski et al. | 604/43 |
| 5,509,900 A | 4/1996 | Kirkman | 604/104 |
| 5,514,112 A | 5/1996 | Chu et al. | 604/267 |
| 5,518,498 A | 5/1996 | Lindenberg et al. | 600/30 |
| 5,522,400 A | 6/1996 | Williams | 128/772 |
| 5,571,093 A | 11/1996 | Cruz et al. | 604/270 |
| 5,681,280 A | 10/1997 | Rusk et al. | 604/95 |
| 5,702,365 A | 12/1997 | King | 604/105 |
| 5,713,853 A | 2/1998 | Clark et al. | 604/53 |
| 5,749,826 A | 5/1998 | Faulkner | 600/29 |
| 5,817,067 A | 10/1998 | Tsukada | 604/256 |
| 5,857,464 A | 1/1999 | Desai | 128/658 |
| 5,885,258 A | 3/1999 | Sachdeva et al. | 604/281 |
| 5,888,196 A | 3/1999 | Bonutti | 600/204 |
| 5,957,900 A | 9/1999 | Ouchi | 604/264 |
| 6,001,079 A | 12/1999 | Pourchez | 604/43 |
| 6,033,397 A | 3/2000 | Laufer et al. | 606/27 |
| 6,052,612 A | 4/2000 | Desai | 600/435 |
| 6,071,263 A | 6/2000 | Kirkman | 604/104 |
| 6,177,049 B1 | 1/2001 | Schnell et al. | 422/44 |
| 6,179,813 B1 * | 1/2001 | Ballow et al. | 604/164.01 |
| 6,238,412 B1 | 5/2001 | Dubrul et al. | 606/200 |
| 6,270,490 B1 | 8/2001 | Hahnen | 604/509 |
| 6,283,940 B1 | 9/2001 | Mulholland | 604/96.01 |
| 6,293,958 B1 | 9/2001 | Berry et al. | 606/191 |
| 6,336,933 B1 | 1/2002 | Parodi | 606/139 |
| 6,409,700 B1 | 6/2002 | Siegel, Jr. et al. | 604/43 |
| 6,454,775 B1 | 9/2002 | Demarais et al. | 606/128 |
| 6,461,321 B1 | 10/2002 | Quinn | 604/43 |
| 6,475,207 B1 | 11/2002 | Maginot et al. | 604/508 |
| 6,482,169 B1 | 11/2002 | Kuhle | 604/6.16 |
| 6,517,529 B1 | 2/2003 | Quinn | 604/528 |
| 6,527,737 B2 | 3/2003 | Kaneshige | 604/48 |
| 6,547,761 B2 | 4/2003 | Liu | 604/104 |
| 6,558,349 B1 | 5/2003 | Kirkman | 604/104 |
| 6,558,350 B1 | 5/2003 | Hart et al. | 604/104 |
| 6,569,150 B2 | 5/2003 | Teague et al. | 604/524 |
| 6,579,302 B2 | 6/2003 | Duerig et al. | 606/198 |
| 6,758,836 B2 | 7/2004 | Zawacki | 604/284 |
| 6,767,339 B2 | 7/2004 | Reydel | 604/175 |
| 6,966,886 B2 | 11/2005 | Appling | 604/6.16 |
| D581,529 S * | 11/2008 | Moehle et al. | D24/130 |
| 2001/0011182 A1 | 8/2001 | Dubrul et al. | 606/200 |
| 2001/0018576 A1 | 8/2001 | Quinn | 604/264 |
| 2002/0026156 A1 | 2/2002 | Quinn | 604/264 |
| 2002/0072768 A1 | 6/2002 | Ginn | 606/213 |
| 2002/0143292 A1 | 10/2002 | Flinchbaugh | 604/107 |
| 2002/0177822 A1 | 11/2002 | St. Cyr et al. | 604/264 |
| 2003/0032918 A1 | 2/2003 | Quinn | 604/43 |
| 2003/0093029 A1 * | 5/2003 | McGuckin et al. | 604/43 |
| 2003/0139763 A1 | 7/2003 | Duerig et al. | 606/198 |
| 2005/0033264 A1 * | 2/2005 | Redinger | 604/523 |
| 2005/0148929 A1 | 7/2005 | Gingles | 604/95.04 |
| 2005/0177094 A1 * | 8/2005 | Igarashi et al. | 604/43 |
| 2005/0261663 A1 | 11/2005 | Patterson et al. | 604/508 |
| 2006/0253063 A1 | 11/2006 | Schweikert | 604/30 |
| 2007/016124 A1 | 1/2007 | McGraw | 604/4.01 |

FOREIGN PATENT DOCUMENTS

| | | |
|---|---|---|
| WO | WO 02/064202 A3 | 8/2002 |
| WO | WO 2005/049125 A1 | 6/2005 |
| WO | WO 2006/002192 A | 1/2006 |

* cited by examiner

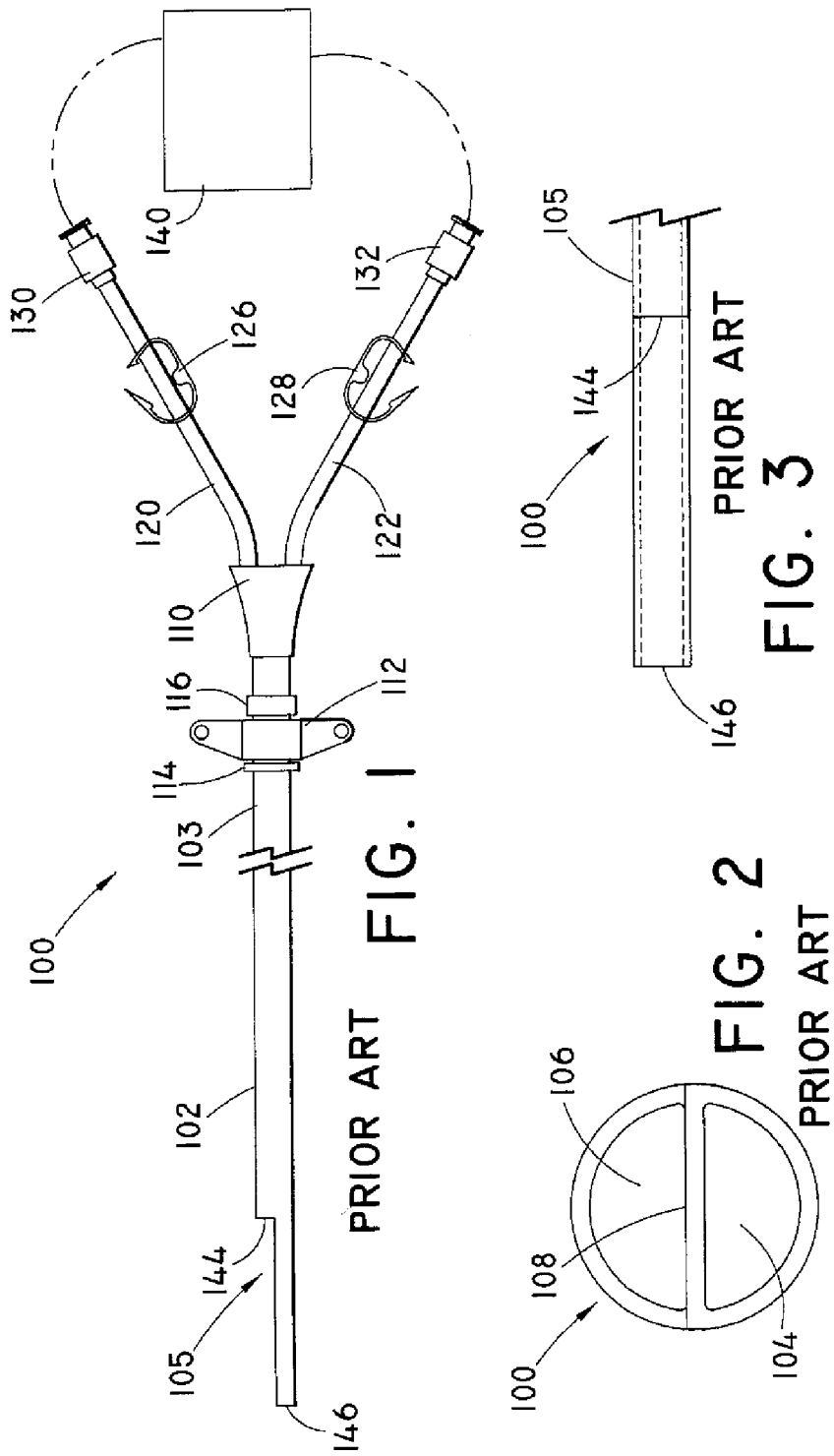

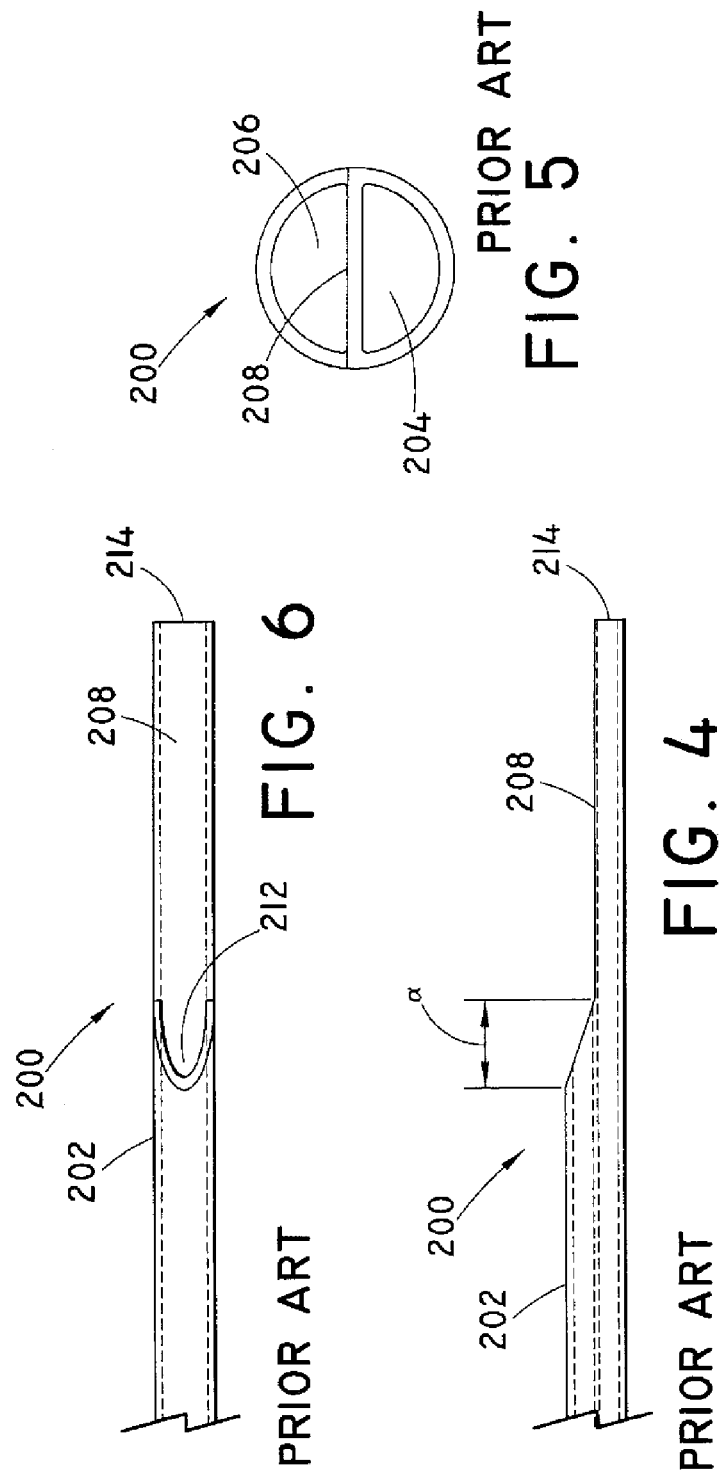

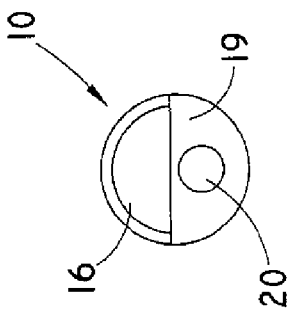
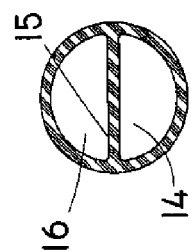
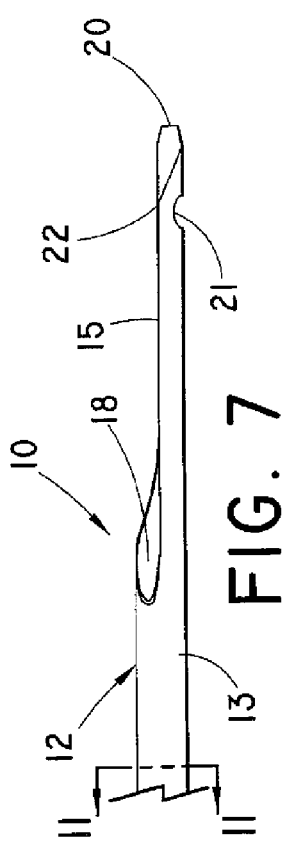
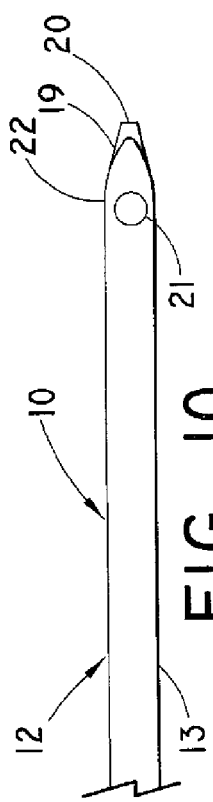
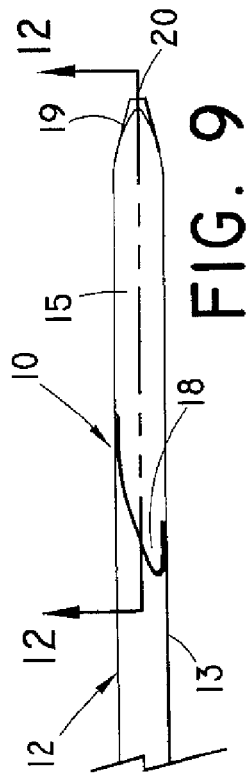
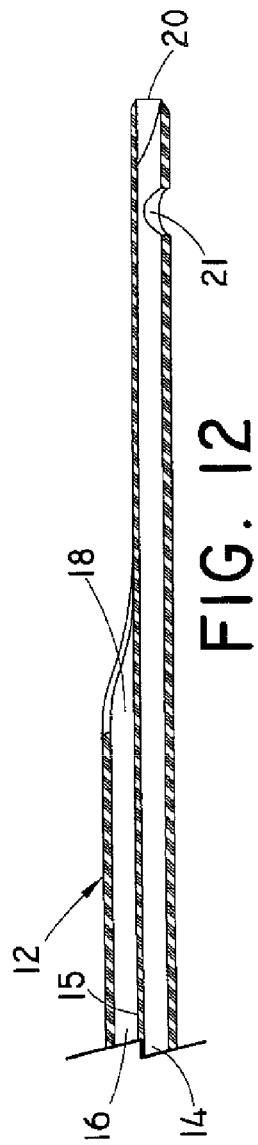

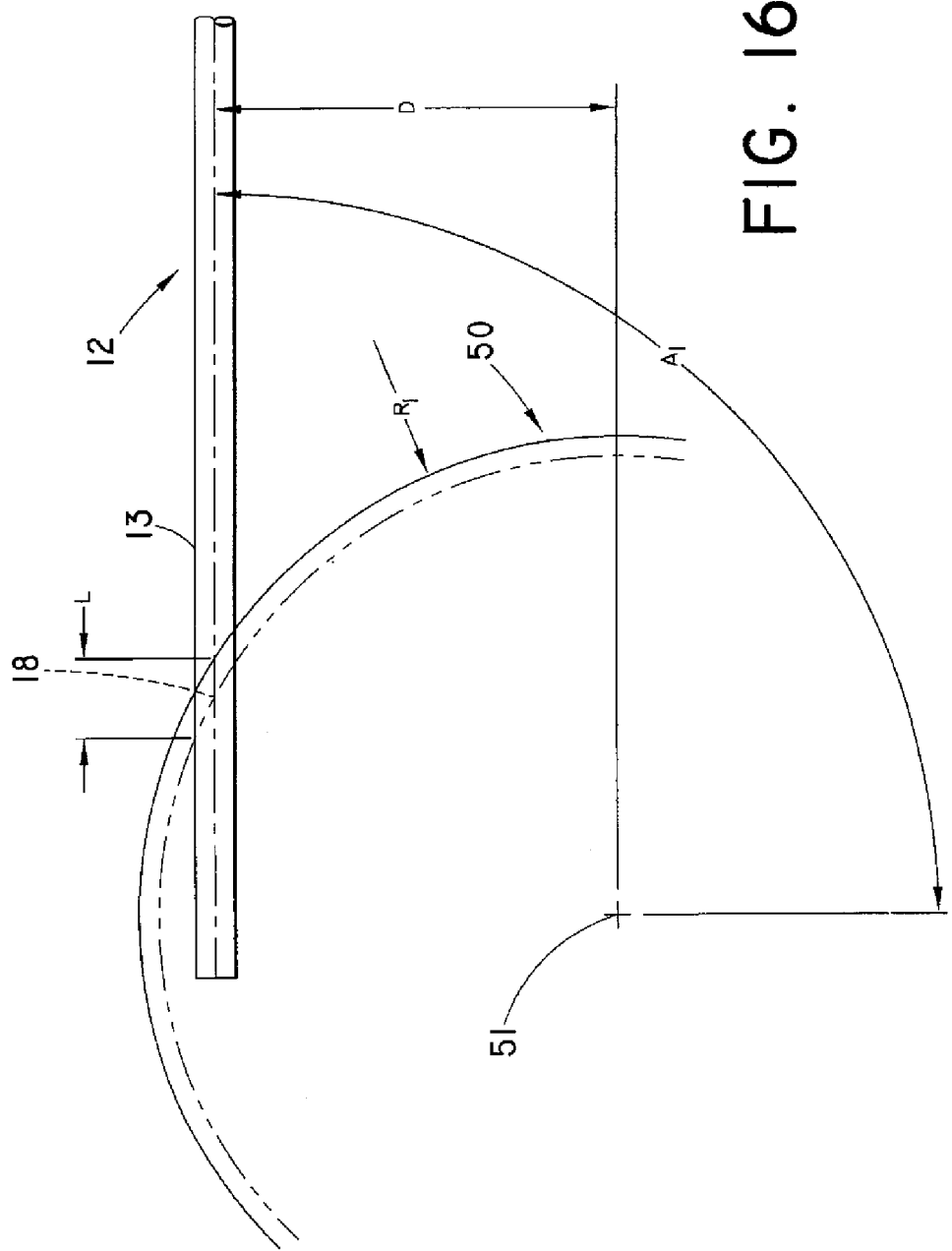

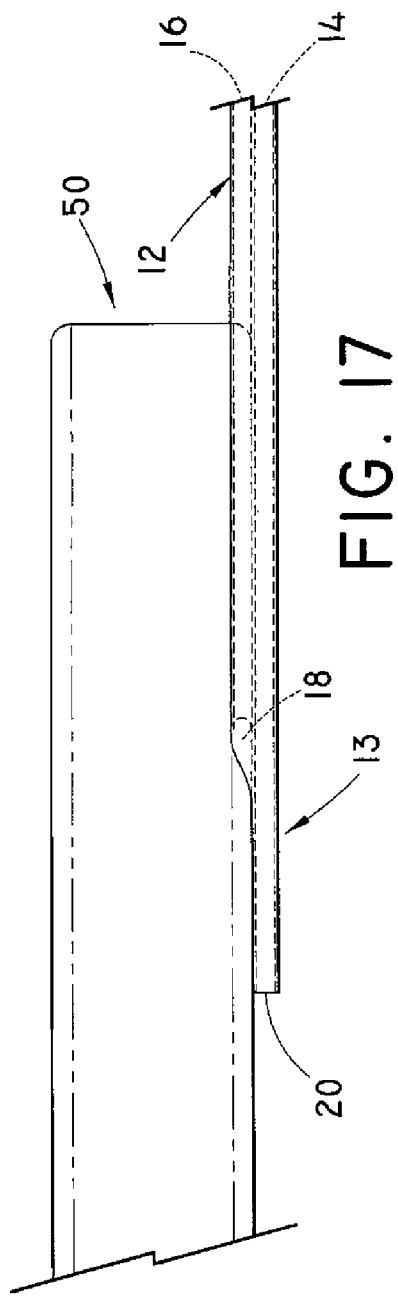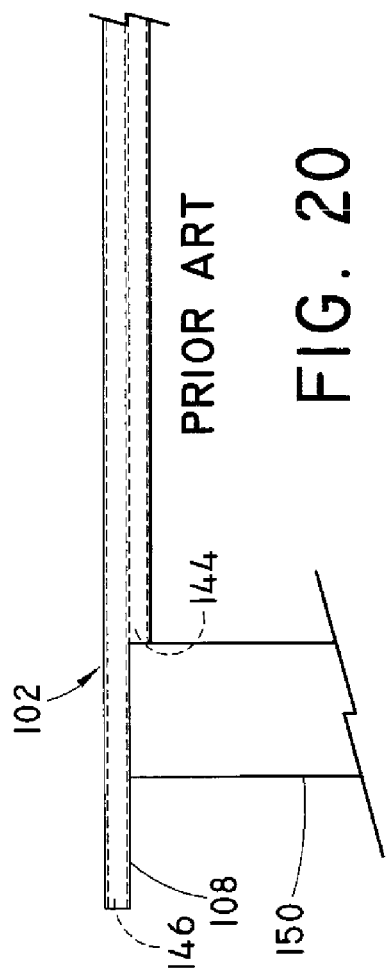

CATHETER PORT CONFIGURATION

RELATED APPLICATION

The present patent document claims the benefit of the filing date under 35 U.S.C. §119(e) of Provisional U.S. Patent Application Ser. No. 60/854,515, filed Oct. 26, 2006, which is hereby incorporated by reference.

BACKGROUND

1. Technical Field.

The present application relates generally to a medical device, such as a catheter, for use in transporting fluids. More particularly, the application relates to a dual lumen catheter for transporting a bodily fluid for extracorporeal treatment, and returning the treated fluid to the body.

2. Background Information.

Dual lumen catheters are commonly used for transporting a bodily fluid for treatment external of the patient's body, a process generally referred to in the medical field as "extracorporeal" treatment, and thereafter returning the treated fluid to the body. A fluid is withdrawn from the body through one of the lumens of the catheter, generally referred to as the withdrawal lumen. The fluid is subjected to a treatment process, and thereafter returned (or "infused") to the body through the other lumen, generally referred to as the infusion lumen.

In many cases, the extracorporeal treatment is carried out as part of a hemodialysis procedure. During hemodialysis, blood is withdrawn from a blood vessel through the withdrawal lumen and routed to a dialyzer for cleansing. The cleansed blood is then returned to the blood vessel through the infusion lumen. When such a catheter is used for hemodialysis, it is generally inserted into the body through the jugular vein, the subclavian vein or the femoral vein. In addition to hemodialysis, extracorporeal catheters can also be used for other procedures in which a fluid is removed from the body for treatment and later returned to the body.

A variety of hemodialysis catheters are available. Among the types of commercially available catheters are: 1) a dual lumen catheter having one lumen (e.g., the blood infusion lumen), that terminates distal to the other lumen (e.g., the blood withdrawal lumen). Some catheters of this type are provided with a midline split (e.g., the Uldall catheter), while others do not have such a split (e.g., the COOK® DDS catheter); 2) a catheter having a slitted valve in the distal tip that acts as a pressure valve opening. This valve opens inwardly for blood aspiration, outwardly for blood infusion, and remains closed when not in use (e.g., the Groshong catheter); 3) polyester-cuffed central venous silicone catheters that are tunneled underneath the skin to reduce infection (e.g., Broviac, Leonard and Hickman catheters); 4) a dual lumen catheter having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); 5) a dual lumen catheter having a diverting structure consisting of a shoulder that has a straight up distal face and a sloped proximal face to reduce access recirculation and raise pressure in the vicinity of the inlet aperture (U.S. Pat. No. 6,409,700); and 6) a catheter designed for femoral approach having two sets of staggered side ports, resulting in a total of four side ports.

Typically, dual lumen hemodialysis catheters have fixtures and related structure at the proximal end that are larger than the diameter of an introducer device through which the catheter is inserted into the vessel. As a result, splittable introducer sheaths, such as the PEEL-AWAY® introducers commercially available from Cook, Incorporated, of Bloomington, Ind., are often utilized for insertion of the catheter. Although such introducers are generally effective for such use, it would be desirable if the catheter insertion procedure could be simplified in a manner such that a separate introducer sheath would not be required. Eliminating the introducer device simplifies the procedure by omitting the sheath removal step that must otherwise be carried out by the physician, and also reduces the overall cost of the procedure. However, since many conventional hemodialysis catheters have stepped or otherwise non-tapered distal (e.g., entry) portions, these catheters are generally not amenable to non-traumatic insertion in the vessel without the use of a tapered introducer and/or dilator.

It would be desirable to provide a dual lumen catheter for use in the extracorporeal transport of bodily fluids that is capable of insertion into a vessel in substantially non-traumatic fashion, and without the necessity of utilizing an introducer apparatus.

BRIEF SUMMARY

The present invention addresses the shortcomings of the prior art. In one form thereof the invention comprises a catheter for use in the extracorporeal treatment of bodily fluids. The catheter comprises a catheter body having a withdrawal port, an infusion port, and a plurality of lumens therein. One of the lumens comprises a withdrawal lumen for transport of fluids withdrawn from a body vessel through the withdrawal port to an extracorporeal treatment unit, such as a dialyzer. Another lumen comprises an infusion lumen for infusion of treated fluids from the extracorporeal treatment unit through the infusion port into the vessel. A portion of one of the ports, such as the withdrawal port, defines a generally helical profile.

In another form thereof, the present invention comprises a catheter for use in the extracorporeal treatment of bodily fluids. The catheter comprises an elongated generally cylindrical catheter body having a proximal end and a distal end, wherein the distal end tapers to a distal tip portion. The catheter body has a withdrawal port, an infusion port, and a pair of lumens extending therein. One of the lumens comprises a withdrawal lumen for transport of fluids withdrawn from a body vessel through the withdrawal port to a treatment unit, and the other lumen comprises an infusion lumen for infusion of treated fluids from the treatment unit through the infusion port into the vessel. The withdrawal port defines a generally helical profile.

In yet another form thereof, the invention comprises a method for treating a body fluid. A catheter is provided for transporting the body fluid. The catheter comprises a generally cylindrical catheter body having a proximal end and a distal end. The distal end tapers to a distal tip portion, and has a plurality of lumens extending therein. The catheter body has a withdrawal port in communication with a first lumen for transporting fluid withdrawn from a body vessel. The withdrawal port has a generally helical profile, and has an infusion port in communication with a second lumen for returning fluid to the vessel. The distal end of the catheter is inserted into the vessel, and the body fluid to be treated is withdrawn from the vessel through the withdrawal port. The withdrawn fluid is transported through the first lumen to a treatment instrument, such as a dialyzer. The fluid is treated in the treatment instrument, and transported from the treatment instrument through the second lumen. The treated fluid is then infused into the body vessel through the infusion port.

BRIEF DESCRIPTION OF THE DRAWINGS

FIG. 1 is a side elevational view of a prior art hemodialysis catheter assembly;

FIG. 2 is a distal end view of the prior art catheter assembly of FIG. 1;

FIG. 3 is a top view of the distal end portion of the prior art catheter assembly of FIG. 1;

FIG. 4 is a side elevational view of the distal end portion of another prior art hemodialysis catheter assembly;

FIG. 5 is a distal end view of the prior art catheter assembly of FIG. 4;

FIG. 6 is a top view of the distal end portion of the prior art catheter assembly of FIG. 4;

FIG. 7 is a side elevational view of the distal end portion of a catheter according to an embodiment of the present invention;

FIG. 8 is a distal end view of the catheter of FIG. 7;

FIG. 9 is a top view of portion of the catheter of FIG. 7;

FIG. 10 is a bottom view of the catheter of FIG. 7;

FIG. 11 is a transverse sectional view taken along line 11-11 of FIG. 7;

FIG. 12 is a longitudinal section view taken along line 12-12 of FIG. 9;

FIG. 16 is a side view of a portion of the grinding wheel illustrating the spatial relationship with the distal end of the catheter during the grinding process;

FIG. 17 is a top view of the embodiment shown in FIG. 16, wherein the catheter material distal to the helical opening has been ground away;

FIG. 20 is a view showing the use of a grinding wheel to cut the proximal port in the prior art catheter of FIG. 1.

DETAILED DESCRIPTION OF THE DRAWINGS AND THE PRESENTLY PREFERRED EMBODIMENTS

Figure 15:
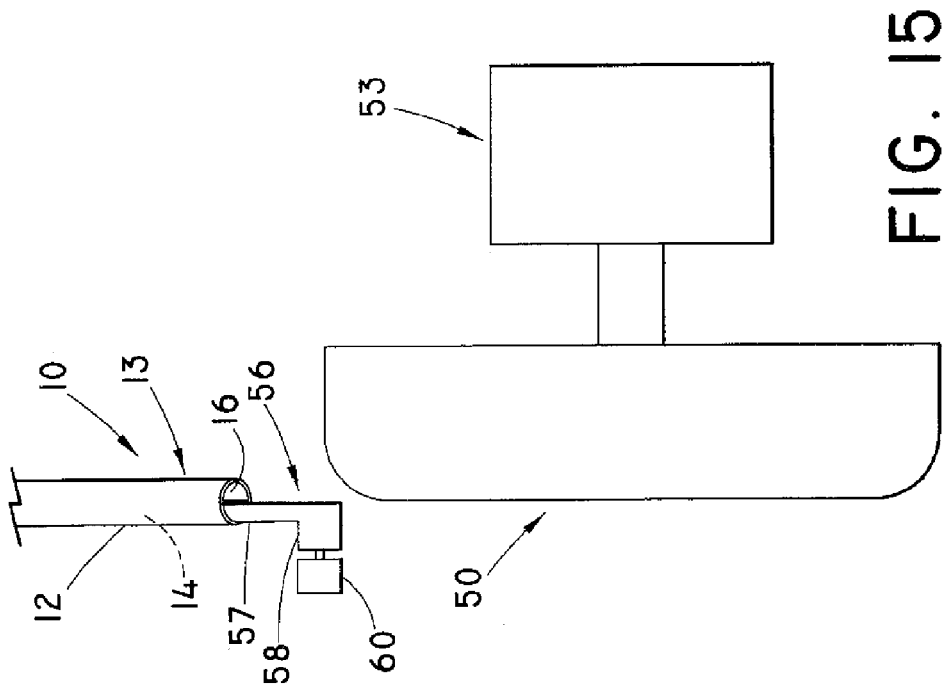
FIG. 15 is a view showing an alignment of the grinding wheel with the elongated catheter body prior to cutting a port having a helical profile into the catheter body.

For purposes of promoting an understanding of the present invention, reference will now be made to the embodiments illustrated in the drawings, and specific language will be used to describe the same. It is nevertheless to be understood that no limitation of the scope of the invention is thereby intended, the scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention is directed to a catheter for use in the transport of bodily fluids for treatment external of the body, referred to in the medical arts as "extracorporeal" treatment. The bodily fluids are transported from the body through a withdrawal lumen in the catheter, and are thereafter transported to an instrument for extracorporeal treatment. The treated fluids are then returned, or infused, to the body through an infusion lumen in the catheter.

Those skilled in the art will appreciate that the catheter described herein is suitable for multiple uses involving inflow and outflow of bodily fluids. However, the invention will be primarily described hereinafter with reference to one of its intended uses, namely as a hemodialysis catheter for use in the extracorporeal treatment of blood. The hemodialysis catheter enables blood inflow without disturbance, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such additional procedures.

In the following discussion, the terms "proximal" and "distal" will be used to describe the axial ends of the catheter, as well as the axial ends of various component features. The "proximal" end is used in conventional manner to refer to the end of the catheter (or component) that is closest to the operator during use of the assembly. The "distal" end is used in conventional manner to refer to the end of the catheter (or component) that is initially inserted into the patient, or that is closest to the patient.

FIG. 1 is a side elevational view of a prior art hemodialysis catheter assembly 100. FIG. 2 is an end view taken from the distal end of prior art catheter assembly 100. FIG. 3 is a top view of the distal end portion of the catheter assembly 100. Prior art assembly 100 includes an elongated generally cylindrical catheter body 102 having a proximal end 103 and a distal end 105, and having dual lumens 104, 106 extending therethrough. Lumen 104 is separated from lumen 106 by septum 108. Catheter assembly 100 includes a conventional bifurcated fitting at its proximal end, such as manifold 110. Manifold 110 may be provided with conventional suture wings 112 if desired. Stop mechanisms 114, 116 may be provided at each axial side of suture wings 112 to prevent catheter body 102 from axial movement relative to the suture wings. Flexible extension tubes 120, 122 extend in the proximal direction from manifold 110. Each extension tube is in fluid communication with a separate one of lumens 104, 106. Clamps 126, 128 are provided for selectively closing off fluid flow through the respective extension tubes 120, 122. Luer lock or other suitable connecting mechanisms 130, 132 are provided for engagement with a treatment instrument 140, such as a dialyzer, for establishing a flow path of blood to and from the dialyzer. Dialyzer 140 and its ingress and egress openings are shown schematically in FIG. 1.

In the prior art hemodialysis catheter assembly 100 shown in FIGS. 1-3, catheter body 102 includes a stepped axial surface along the length of catheter body distal end portion 105. Withdrawal port 144 communicates with lumen 106 for transporting fluid withdrawn from the body vessel through the catheter assembly to the dialyzer. Treated fluid returns from the dialyzer through lumen 104, and is returned to the vessel via infusion port 146. Typically, withdrawal port 144 is proximal to infusion port 146. This arrangement reduces recirculation during hemodialysis, and increases the efficiency of the procedure since cleansed blood that has been returned to the vessel is not immediately withdrawn again and transported to the dialyzer for cleaning. However, this arrangement is not required in all instances, and the withdrawal port may be the more distal port if desired. Ports 144, 146 define a stepped arrangement, wherein port 144 is oriented substantially perpendicular to the vessel wall upon insertion of the apparatus. This orientation is advantageous since it makes it difficult for the wall to collapse over the opening in the port and block the flow of blood.

Another prior art hemodialysis catheter assembly 200 is shown in FIGS. 4-6. FIG. 4 is a side elevational view of the distal end portion of prior art hemodialysis catheter assembly 200. FIG. 5 is an end view taken from the distal end of the catheter assembly 200, and FIG. 6 is a top view of the portion of the prior art catheter assembly shown in FIG. 4. The proximal portion of assembly 200 may be the same or similar to that of prior art assembly 100, and need not be further shown or described to attain an understanding of the present invention.

Prior art assembly 200 includes an elongated generally cylindrical catheter body 202, and has dual lumens 204, 206 extending therethrough. Lumen 204 is separated from lumen 206 by septum 208. Withdrawal port 212 communicates with lumen 206 for transporting fluid withdrawn from the vessel through the catheter assembly to the dialyzer. Treated fluid returns to the vessel through lumen 204 and infusion port 214, in the same manner described with reference to the prior art embodiment of FIGS. 1-3.

Unlike the stepped arrangement of the ports of prior art assembly 100, withdrawal port 212 of prior art assembly 200 comprises a straight angled cut. This is best visualized at FIG. 4 by reference symbol $\alpha$. This design has a more tapered distal portion than the stepped arrangement of assembly 100, and allows for easier insertion into the vessel. However, the straight angled arrangement defined by straight angled cut $\alpha$ exposes a greater portion of the opening to the vessel wall, thereby increasing the possibility of blockage of the withdrawal port. On the other hand, the stepped arrangement of assembly 100 (FIGS. 1-3) minimizes the possibility of blockage. However, the assembly having the stepped arrangement cannot be inserted without the use of a removable sheath, such as the splittable sheaths discussed above.

FIG. 7 is a side elevational view of the distal end portion 13 of a catheter 10 according to an embodiment of the present invention. FIG. 8 is an end view of the catheter of FIG. 7. FIG. 9 is a top view of distal end portion 13 of the catheter of FIG. 7, and FIG. 10 is a bottom view of catheter distal end portion 13. The proximal portion of catheter 10 is conventional, and need not be further shown and described to attain an understanding of the inventive features of the present invention.

Catheter 10 includes an elongated generally cylindrical catheter body 12 having lumens 14, 16 extending at least partially therethrough. Preferably, catheter body 12 tapers to a tip portion 19. Lumens 14, 16 are separated by a septum 15. FIGS. 11 and 12 are respective transverse and longitudinal sectional views taken through catheter body 12. Catheter body 12 may be formed from a conventional polymer commonly used in the medical arts for such purposes, such as radiopaque polyurethane. Other conventional materials used for such purposes in the medical arts may be substituted. Non-limiting examples of such materials include silicone, polyurethane and PTFE.

As illustrated, withdrawal port 18 communicates with lumen 16 for transporting fluid withdrawn from the vessel through the catheter assembly to the dialyzer (not shown) for treatment. Treated fluid returns to the vessel through lumen 14 and at least one infusion port. In the preferred embodiment shown, two infusion ports 20, 21 are provided for receiving treated fluid and through which the treated fluid passes into the vessel. Infusion port 20 is positioned at the distal end of tapered tip portion 19. Infusion port 21 is provided along the bottom of catheter body 12. Preferably, infusion port 21 is spaced about 1 mm proximal to a transition point 22 between the main catheter body portion and the tapered tip 19. Port 21 is provided to prevent the infusion flow rate from being reduced due to the reduction in cross-sectional area of lumen 14 distal of transition point 22. Preferably, the total cross-sectional area of infusion ports 20 and 21 is greater than that of the infusion lumen to insure smooth flow through the infusion lumen, and to inhibit the likelihood of fluid back-up in lumen 14. Although two infusion ports are illustrated in the embodiment shown herein, those skilled in the art will appreciate that more, or fewer, infusion ports can be provided in the catheter body if desired.

Insertion of the catheter into the vessel can be made over a wire guide, e.g., via the well-known Seldinger percutaneous entry technique. Transport of bodily fluid to the dialyzer and return of the treated fluid to the body vessel follows a path substantially similar to that of the prior art embodiments described, and need not be further described.

Unlike the stepped withdrawal port 144 of the prior art design shown in FIGS. 1-3, and the straight angle withdrawal port 212 of the prior art design shown in FIGS. 4-6, the withdrawal port 18 of catheter 10 comprises a substantially helically-shaped cut along a portion of the distal outer surface of catheter body 12. As a result, the design combines the beneficial features of the respective stepped and straight angled prior art designs described above, while substantially avoiding the disadvantages of said prior art designs.

In one preferred embodiment, tapered portion 19 extends in the proximal direction from infusion port 20 to transition point 22 a distance of about 8 mm at the furthest points, and about 3 mm in the center. In the non-limiting embodiment described, the helical cut preferably commences about 30 mm proximal to the transition point 22, and extends in the proximal direction a distance of about 5 to 15 mm, preferably about 10 mm. In the preferred embodiment described, the infusion lumen 14 and the port opening 20 at the distal tip are not coaxial with the center axis of the catheter body. In this case, the transition is generally in the shape of a parabola. Following dilation of the tissue in conventional fashion, the combination of the tapered distal end and the helical cut design provides a generally smooth insertion surface that eliminates the need for an introducer sheath, such as the splittable introducer sheath discussed above.

Unlike the angled design of FIGS. 4-6, the helically-shaped cut of the inventive design is advantageous because the opening of the helical cut port remains primarily perpendicular to the vessel wall. This arrangement provides support for the vessel wall, making it more difficult for the wall to collapse over the port opening and block blood flow. As stated, the tapered distal end portion of the catheter also constitutes an improvement over the stepped wall design of FIGS. 1-3, because it allows the assembly to be inserted without the necessity of using a separate introducer sheath.

Those skilled in the art will appreciate that there are numerous ways in which a helical cut can be made in a catheter or like device. In one preferred method, the cuts are made with a conventional cutting fixture, such as a grinder or a razor blade, in a similar manner to other cuts that have been made in prior art devices. For example, the stepped port in prior art assembly 100 may be cut by aligning a grinding wheel 150 in a manner such that the axis of the grinding wheel is positioned parallel to the cylindrical catheter body 102. This is shown in FIG. 20. The edge of grinding wheel 150 has a very small radius, and tubular body 102 is fed along the outer edge of the grinding wheel such that only one lumen is exposed to the grinding wheel. This results in an offset proximal port 144 with the port opening generally perpendicular to the catheter axis. This angle could be increased by feeding the catheter at various angles; however, the cut port surface is always in a single plane.

When a razor blade or other straightedge is used to cut the proximal (withdrawal) port, the blade can be used to remove all of the material distal to the withdrawal port, or alternatively, only the port material if the catheter is initially ground using the process described above. A Jig may be used to guide the blade and prevent unintended removal of material. In this process, the blade can be held perpendicular to the septum of the catheter body while being rotated, or can be rotated and tilted proximally to create a ramp-like shape.

Figure 14:
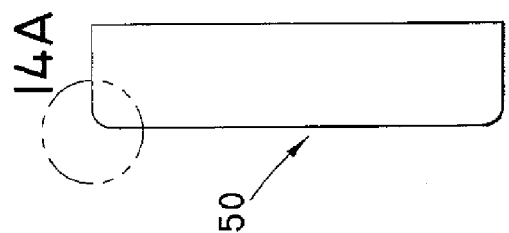
FIG. 14 is a side view of the grinding wheel of FIG. 13.
Figure 13:
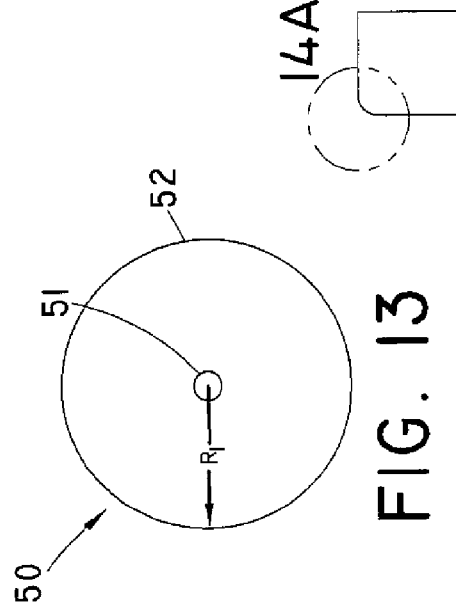
FIG. 13 is a front view of a grinding wheel for use in forming a catheter port according to an embodiment of the present invention.
Figure 14A:
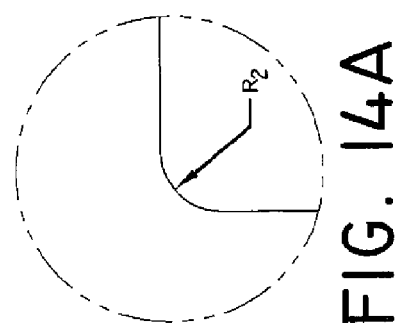
FIG. 14A is an enlarged view of an edge portion of the grinding wheel shown in FIG. 14.

A preferred cutting device includes a grinding wheel having dual radii. Having two different radii enables the operator to accurately provide predetermined dimensions on the catheter body for both the length and the longitudinal curvature of the helical port of the catheter. FIG. 13 illustrates a front, or face, view of a grinding wheel 50 of a type that may be utilized to form the helical port. Grinding wheel 50 includes a radius $R_1$ that extends from the radial center 51 of the grinding wheel to the outer circumference 52 of the wheel. Grinding wheel 50 also includes a corner radius $R_2$. This radius is shown in FIG. 14, and in the expanded view of FIG. 14A. Radius R2 determines the longitudinal curvature of the helix. Further discussion of R1 and R2 and their significance in determining the dimensions of the cut are provided below. A conventional power source, such as grinder motor 53, is provided for rotating grinder wheel 50.

To form the helical cut utilizing grinding wheel 50, an elongated pin 56 having substantially the same general cross-sectional dimension as lumen 14 is preferably inserted into lumen 14. This is shown in FIG. 15. In one preferred embodiment, the spacing between the distal and proximal ports is about 3 cm. In this case, the pin extends into the catheter tube about 1 cm beyond this spacing, or in other words, about 4 cm into the tube from the distal end of the catheter. This length will enable the pin to provide rigidity to the catheter during the helical cutting process. For manufacturing purposes, it is generally preferred to have a shorter length pin, such as the pin described, since it requires less time inserting and removing the pin from the catheter. Alternatively, a longer pin could be used, however the additional length provided by such a pin is generally unnecessary.

In the example shown, pin 56 includes an elongated main body 57 and a head 58 extending substantially perpendicular from main body 57. Head 58 of pin 56 is engaged in any conventional manner with a conventional pivot assembly 60, in a manner such that pin 56 is at least partially pivotable about pivot assembly 60. Those skilled in the art are well aware of suitable means of rotation of a pin relative to a pivot assembly, and any such means may be substituted for that described and shown herein.

To cut catheter distal end portion 13, the tubular catheter body 12 is initially aligned with the grinding wheel in the manner shown in FIG. 15. Typically, the pivot assembly 60 is aligned relative to the grinding wheel 50 such that upon pivoting of the tubular catheter body by the operator around the axis of the pivot assembly, the length of the cut can be controlled.

FIGS. 16-19 illustrate in detail one preferred manner in which the helical cut may be formed in catheter body 12. FIG. 16 illustrates a side view of a portion of grinding wheel 50, illustrating the spatial relationship of the grinding wheel with the distal end 13 of catheter body 12 during the grinding process. R1, D and A1 represent parameters that may be adjusted to affect the length L of the helical opening cut into the catheter body. A1 represents the angle between a vertical plane through the central axis of the grinding wheel and the central axis of the catheter body. An angle of 90° would indicate a catheter body aligned horizontal to the grinding wheel. D represents the distance from the radial center 51 of the grinding wheel to the axis of the catheter body. In this case, D must be less than R1, or the catheter body cannot come into contact with the face of the grinding wheel. When A1 is less than 90°, D must be reduced to ensure that the entire distal tip of the catheter body is in contact with the face of the grinding wheel (the distal tip will rotate away from the wheel as A1 is reduced if the catheter axis rotates about the center of the helical port).

Figure 18:
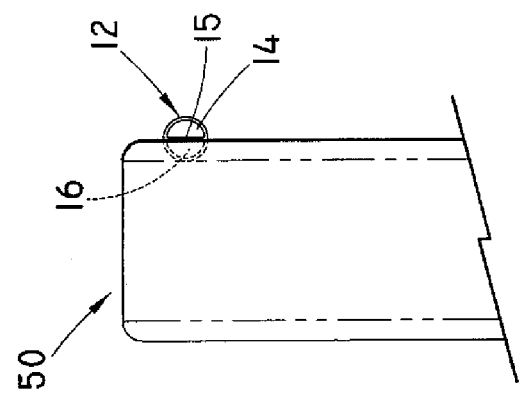
FIG. 18 is an end view of the junction shown in FIG. 16 showing the overlap between the grinding wheel and the distal end of the catheter.
Figure 19:
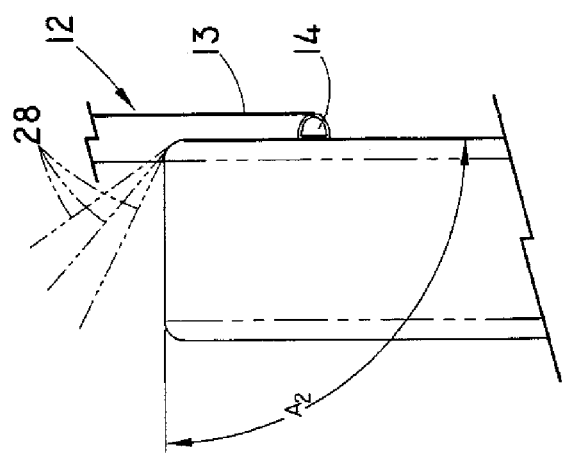
FIG. 19 is an oblique view of FIG. 18 showing the interaction of the radius R2 of the grinding wheel and the impact on the angle A2 of the helical opening.

The features are illustrated in greater detail in FIGS. 17-19. FIG. 17 is a top view of the junction of the grinding wheel 50 and catheter distal end 13 shown in FIG. 16, showing the helical port opening 18 in phantom. As shown in FIG. 17, the catheter material from lumen 16 distal to the helical opening has been cut away.

FIG. 18 is an end view of the junction of the grinding wheel and catheter body end as shown in FIG. 16, illustrating an overlap between the grinding wheel and the distal end of catheter body 12. As shown, the catheter body is positioned such that septum 15 of the catheter body that separates the lumens is nearly flush against the face of the grinding wheel.

FIG. 19 is an oblique view of FIG. 18, indicating the interaction of the radius R2 of the grinding wheel and the impact on the angle A2 of the helical opening. R2 controls the angle of the port opening relative to the catheter septum. A steeper opening is generally preferred to avoid blockage by the vein wall. Ideally R2 will be no larger than the radius of the catheter to keep the opening at 90°. A1 represents the angle between the opening of the helical port and catheter septum 15. Since A2 is preferably 90°, R2 is no larger than the radius of the catheter body. If R2 is larger than this radius, the shape of the helical port will only be a partial radius or arc, and will not be able to follow the radius a full 90°. The angle of the opening can be estimated by lines 28 tangent to the radius, as labeled in FIG. 19.

In theory, a longer port length (L) is preferred for ease of insertion. However, in practice, consideration must also be given to not having an excessively long port, since a longer port length may be more susceptible to clot formation when the catheter is not in use than a shorter port length. Because of the size/shape of the helical opening, a heparin lock of the type that might normally be used between dialysis sessions to inhibit clotting cannot remain in place within the entire opening. Due to the novel helical port shape, the lock can only exist up to the proximal edge of the helical port. Anything distal to that will not be trapped by vacuum within the catheter, and will enter the bloodstream. In addition, contact with the bloodstream will draw off any heparin solution that is exposed to it. Thus, those skilled in the art will recognize that a balance between the use of a heparin lock and the ease of insertion of the catheter must be obtained.

Those skilled in the art will appreciate that the port opening described herein may also be formed by other methods. For example, rather than pivoting the pin as described, the pin can be stationary, and the catheter can be ground as it is slid over the pin. The pin can rotate in a plane parallel to the face of the grinder, as described in the current embodiment, or alternatively, the pin can rotate in a plane perpendicular to the face of the wheel. This arrangement may be advantageous because it would minimize the contact duration between the catheter and the grinder. The longer that the catheter stays in contact with the grinder, the more heat is generated due to friction. This could result in material deformation and/or excess material removal. Alternatively, the majority of the distal tip can be removed in a separate step, with only the details of the helical port being addressed with the process described herein.

Although the port design has been described herein as having a generally helical profile, the helical profile need not necessarily extend the entire length of the port, and beneficial results may be obtained when only a portion of the port includes a generally helically-shaped profile.

It is therefore intended that the foregoing detailed description be regarded as illustrative rather than limiting, and that it be understood that it is the following claims, including all equivalents, that are intended to define the spirit and scope of this invention.

The invention claimed is:

1. A catheter for use in the extracorporeal treatment of bodily fluids, comprising:
an elongated generally cylindrical catheter body configured for sheathless substantially non-traumatic entry into a body vessel, said catheter body having a proximal end and a distal end, said distal end tapering to a distal tip portion suitable for said sheathless substantially non-traumatic entry, said catheter body having a pair of lumens extending therein, said catheter body having a withdrawal port in communication with a first one of said lumens for transporting fluid withdrawn from the body vessel for said treatment, an infusion port in communication with a second one of said lumens for return of treated fluid to the vessel, and a septum separating said first and second lumens, said withdrawal port defining a non-planar longitudinal curvature extending a length of about 5 to 15 mm in the proximal direction from a distal end to a proximal end of said withdrawal port, and wherein said proximal end of said withdrawal port is substantially perpendicular to a wall of said vessel, said withdrawal port being proximal to said infusion port along a length of said catheter body, and wherein said infusion port comprises an opening at said distal tip portion.

2. The catheter of claim 1, wherein said distal tip opening is axially offset from a center axis of the catheter body.

3. The catheter of claim 1, wherein said infusion port comprises a first infusion port, said catheter body further comprising a second infusion port axially spaced from said first infusion port, said second infusion port communicating with said infusion lumen for infusion of treated fluids into the vessel.

4. The catheter of claim 3, wherein each of said first and second infusion ports has a cross-sectional area, and wherein a combined cross-sectional area of said first and second infusion ports is greater than a cross-sectional area of said infusion lumen.

5. The catheter of claim 1, wherein said catheter body is formed from silicone, polyurethane or PTFE.

6. The catheter of claim 1, wherein said withdrawal port extends along said catheter body in an axial direction a distance of about 10 mm.

7. The catheter of claim 1, wherein said distal end tapers a distance of about 8 mm from a transition point along said catheter body to said distal tip portion.

8. The catheter of claim 7, wherein said longitudinal curvature of said withdrawal port commences about 30 mm proximal to said transition point.

9. The catheter of claim 8, wherein said longitudinal curvature extends in the proximal direction a distance of about 10 mm.

10. A method for treating a body fluid, comprising:
providing a sheathless catheter for transporting said body fluid, said catheter comprising a generally cylindrical catheter body having a proximal end, a distal end, a plurality of lumens extending therein, and a septum separating said lumens, said distal end tapering to a distal tip portion, said catheter body having a withdrawal port in communication with a first lumen for transporting fluid withdrawn from a body vessel, said withdrawal port configured for substantially non-traumatic entry into said vessel, said withdrawal port having a longitudinal curvature extending in a proximal direction from said septum along a length of said port to a maximal diameter portion wherein said port is substantially perpendicular to a wall of said vessel, and having an infusion port in communication with a second lumen for returning fluid to said vessel;
effecting substantially non-traumatic percutaneous entry of said sheathless catheter into said vessel by inserting said distal end of said catheter and said withdrawal port directly into said vessel;
withdrawing body fluid to be treated from said vessel through said withdrawal port;
transporting said withdrawn fluid through said first lumen to a treatment instrument;
treating said fluid in said treatment instrument;
transporting said treated fluid from said treatment instrument through said second lumen; and
infusing treated fluid into said body vessel through said infusion port.

11. The method of claim 10, wherein said infusion port comprises an opening at the distal tip of said catheter body, and wherein said catheter body further includes a second infusion port along a length of said body in communication with said second lumen for infusion of treated fluid into said body vessel, each of said first and second infusion ports having a cross-sectional area, and wherein the combined cross-sectional areas of said first and second infusion ports is greater than a cross-sectional area of said second lumen.

12. The method of claim 10, wherein said withdrawal port is proximal to said infusion port along a length of said catheter body.

13. The method of claim 10, wherein said treatment unit comprises a dialyzer.

14. A sheathless catheter for substantially non-traumatic entry into a blood vessel, comprising:
an elongated generally cylindrical catheter body configured for said vessel entry, said catheter body having a proximal portion, a distal portion tapering to a distal tip, a first lumen and a second lumen extending therethrough, and a septum separating the first and second lumens; the catheter body having a withdrawal port in communication with the first lumen, and an infusion port in communication with the second lumen, the withdrawal port defining a non-planar helical profile wherein a first end of the withdrawal port is at a first distance from the distal tip, a second end of the withdrawal port is at a second distance from the distal tip, and an intermediate portion of the withdrawal port between the first and second ends is at a third distance from the distal tip, the first distance being greater than the second distance, and the third distance being greater than the first and second distances, the first and second ends and the intermediate portion of the withdrawal port comprising a substantially non-traumatic curvature along said septum to a maximum radial diameter of said port from said septum, said withdrawal port opening being substantially perpendicular to a wall of the vessel, and wherein the infusion port comprises an opening at the distal tip.

15. The catheter of claim 14, wherein said withdrawal port profile is substantially helical from said first end to said second end, said withdrawal port having a generally smooth taper along said septum from said first end to said intermediate portion, and a generally smooth taper from said intermediate portion to said second end for said substantially non-traumatic entry.

\* \* \* \* \*

UNITED STATES PATENT AND TRADEMARK OFFICE
CERTIFICATE OF CORRECTION

| | | |
|---|---|---|
| PATENT NO. | : 8,545,434 B2 | Page 1 of 1 |
| APPLICATION NO. | : 11/877057 | |
| DATED | : October 1, 2013 | |
| INVENTOR(S) | : Christopher D. Bosel et al. | |

It is certified that error appears in the above-identified patent and that said Letters Patent is hereby corrected as shown below:

On the Title Page
At Item (73)

Delete "Cook Medical Technology LLC" and insert --Cook Medical Technologies LLC--

Signed and Sealed this
Twenty-fifth Day of March, 2014

Michelle K. Lee
*Deputy Director of the United States Patent and Trademark Office*